Aug. 3, 1937. J. SQUARE Plant Pat. 259
ROSE
Filed Sept. 16, 1936
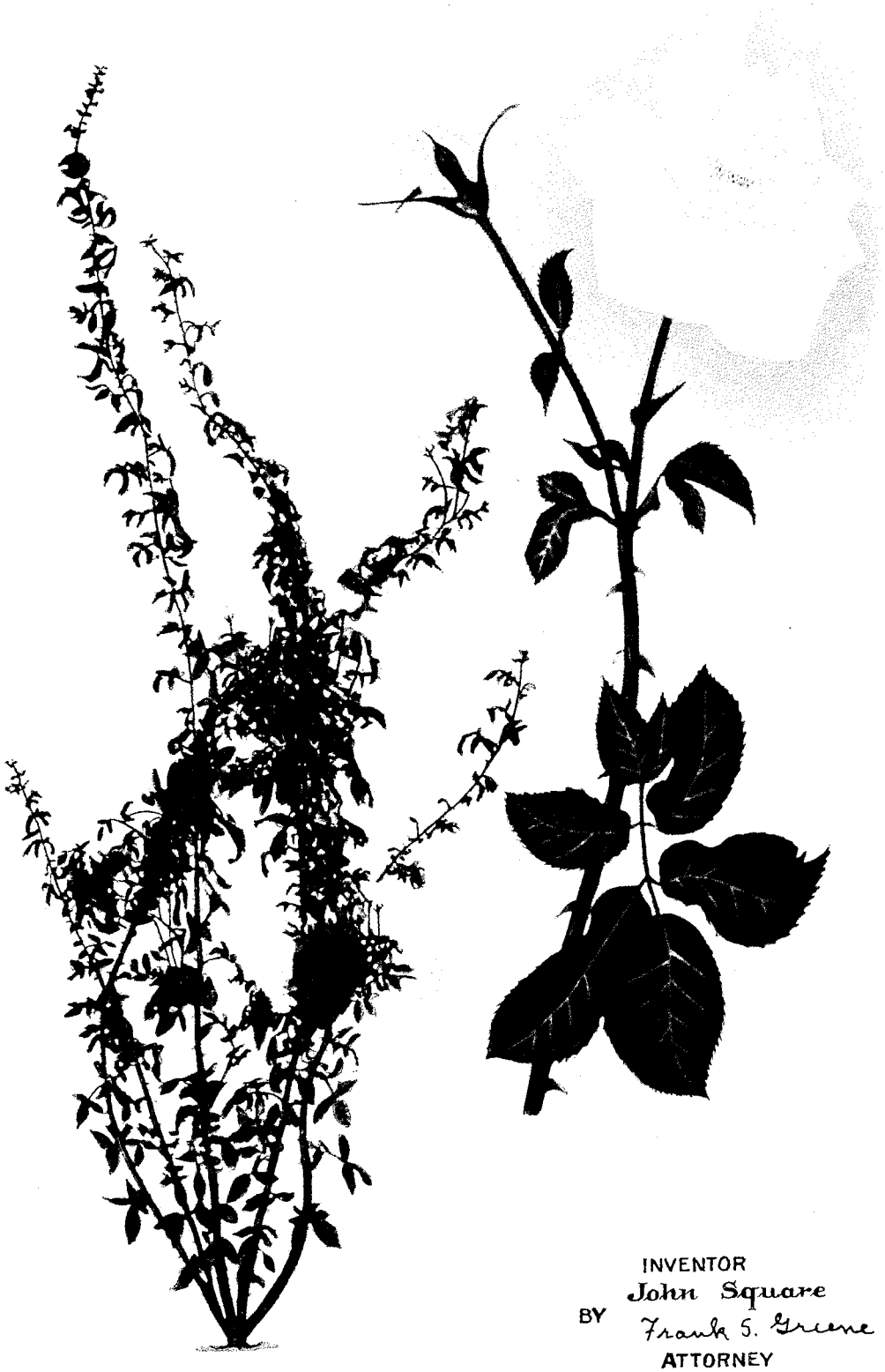
INVENTOR
John Square
BY Frank S. Greene
ATTORNEY Patented Aug. 3, 1937

Plant Pat. 259

UNITED STATES PATENT OFFICE

259

ROSE

John Square, Lake County, Ohio

Application September 16, 1936, Serial No. 101,112

1 Claim. (Cl. 47—61)

This invention relates to a new variety of hybrid tea rose which I have discovered and propagated in my nursery near Painesville, Ohio.

This new variety first appeared as a sport of the Souvenir de Claudius Pernet rose which differed in several important respects from the parent plant. By careful propagation I have succeeded in making permanent the desirable variations and have produced a new variety of rose.

The new variety of rose is a very luxurious pillar rose which is very hardy and which bears large well formed yellow flowers, the plant blooming on the green canes near the tips as well as on the lower portions of the plant.

Compared with its parent, the Souvenir de Claudius Pernet which is a dwarf variety, this new variety is characterized by a much more vigorous growth. The green canes are very much larger and grow in one season to from 6 to 8 feet in height. The flowers are larger, having larger petals and a greater number of petals.

The plants which I am now growing have been blooming profusely throughout the summer and are still blooming in September.

My new variety of rose is very hardy, much hardier than most climbing tea roses, and tea roses, even though it is yellow. Practically all the thousands of plants I am now growing survived the severe cold of the winter of 1935–36 although unprotected in the open field, thus indicating it is sufficiently hardy for northern gardens.

The accompanying drawing shows one of the plants of the new variety and alongside the plant a substantially full size view of a bud, a flower and a short length of stem with the foliage thereon.

The plant shown in the drawing is as it appeared during the last week in August of this year. This plant, which is a typical example of the new variety of rose now being grown by me, was budded in the summer of 1935 and the entire plant is this year's growth. The three longest canes are from 6 to 8 feet in length. The canes are quite thick and strong and require but little support. The foliage is abundant and the growth is upright and very vigorous.

The plant is very thorny, the cane having closely spaced, very stiff, broad based reddish brown thorns, the flower stems being covered with fine thorns, the leaf petioles having closely spaced, fairly stiff and sharp thorns which are brown at the tip and even the leaf rachises having fine thorns.

The leaves are odd pinnate, most of the leaves having seven leaflets. The individual leaflets are serrate and of large size, having a tendency to curl, and are dark green in color and glossy.

The bud is large and long pointed and the portions of the outer petals which show outwardly of the calyx often have streaks of red which disappear as the flower opens.

The flower is a large full double rose of sunflower yellow color which is quite fragrant and which has excellent lasting qualities. The flowers are borne singly, the petals cling, and the blooming is continuous throughout the growing season. The flower has from 40 to 55 well formed petals and opens evenly. The petals have a deeper shade of yellow near their base and the center of the flower is of deeper shade than the outer portion. The central petals cluster over the stamens and conceal them until the flower is fully opened. As compared with the Souvenir de Claudius Pernet rose grown in the same soil under the same conditions, the petals of my new variety of rose are much larger and considerably greater in number. The color of the flower is not distinguishable from that of a Souvenir de Claudius Pernet rose.

As will be seen from the drawing, the plant blooms profusely during its first season of growth and bears flowers high up on the green canes.

It will be apparent that my new variety of rose has several unique and valuable characteristics. One of the most important characteristics is a hardiness exceptional for a climbing hybrid tea rose plant which makes it suitable for gardens in the northern parts of the United States. It is more hardy than most climbing roses bearing large flowers and especially than climbing tea roses with yellow flowers.

Other important characteristics of my new variety of rose plant are its very luxuriant growth, its profuse and recurrent blooming, its recurrent blooming during its first year of growth, the flowering high up on the green canes, and the beauty and fragrance of the flower.

What I claim is:

A rose plant such as herein shown and described characterized by its hardiness, its luxurious growth and climbing tendencies, its large double yellow flower, its recurrent blooming, and its blooming high up on green canes.

his
JOHN × SQUARE.
mark

Witnesses to mark of John Square:
RALPH W. WILKINS,
HELLEN C. SULLIVAN.